(12) United States Patent
Hon

(10) Patent No.: US 8,375,957 B2
(45) Date of Patent: Feb. 19, 2013

(54) ELECTRONIC CIGARETTE

(75) Inventor: Lik Hon, Hong Kong (CN)

(73) Assignee: Ruyan Investment (Holdings) Limited, North Point (HK)

( * ) Notice: Subject to any disclaimer, the term of this patent is extended or adjusted under 35 U.S.C. 154(b) by 0 days.

(21) Appl. No.: 12/226,819

(22) PCT Filed: May 15, 2007

(86) PCT No.: PCT/CN2007/001576
§ 371 (c)(1),
(2), (4) Date: Jan. 15, 2009

(87) PCT Pub. No.: WO2007/131450
PCT Pub. Date: Nov. 22, 2007

(65) Prior Publication Data
US 2009/0126745 A1    May 21, 2009

(51) Int. Cl.
*A24F 1/22* (2006.01)
(52) U.S. Cl. .... 131/194; 131/271; 131/273; 128/202.21
(58) Field of Classification Search .................. 131/194, 131/273, 271; 128/202.21
See application file for complete search history.

(56) References Cited

U.S. PATENT DOCUMENTS

| | | | |
|---|---|---|---|
| 1,775,947 | A | 5/1927 | Robinson |
| 2,057,353 | A | 10/1936 | Whittemore |
| 2,631,219 | A | 3/1953 | Suchy |
| 3,200,819 | A | 8/1965 | Gilbert |
| 4,171,000 | A | 10/1979 | Uhle |
| 4,228,925 | A | 10/1980 | Mendelovich |
| 4,641,053 | A | 2/1987 | Takeda |
| 4,735,217 | A | 4/1988 | Gerth |
| 4,756,318 | A | 7/1988 | Clearman |
| 4,771,796 | A | 9/1988 | Myer |
| 4,819,665 | A | 4/1989 | Roberts |
| 4,848,374 | A | 7/1989 | Chard |
| 4,945,929 | A | 8/1990 | Egilmex |
| 4,945,931 | A | 8/1990 | Gori |

(Continued)

FOREIGN PATENT DOCUMENTS

| | | | |
|---|---|---|---|
| CA | 2562581 | * | 10/2005 |
| CN | 2047485 U | | 11/1989 |

(Continued)

OTHER PUBLICATIONS

"TechPowerUp", "What is a MOSFET, what does it look like, and how does it work?", http://www.techpowerup.com/articles/overclocking/voltmods/21, dated May 24, 2004, printed from the Internet of Jun. 4, 2011, 3 pages.*

(Continued)

*Primary Examiner* — Richard Crispino
*Assistant Examiner* — Dionne Walls Mayes
(74) *Attorney, Agent, or Firm* — Perkins Coie LLP

(57) ABSTRACT

An emulation aerosol sucker includes a battery assembly, an atomizer assembly and a cigarette bottle assembly. An external thread electrode is located in one end of battery assembly. An internal thread electrode is located in one end of atomizer assembly. Said battery assembly and said atomizer assembly are connected by the screwthread electrode. Said cigarette bottle assembly is inserted into the other end of said atomizer assembly and both form one cigarette type or cigar type body.

24 Claims, 10 Drawing Sheets

U.S. PATENT DOCUMENTS

| | | | |
|---|---|---|---|
| 4,947,875 A | 8/1990 | Brooks | |
| 5,042,470 A | 8/1991 | Kanesaka | |
| 5,060,671 A | 10/1991 | Counts et al. | |
| 5,080,114 A | 1/1992 | Rudolph et al. | |
| 5,095,921 A | 3/1992 | Losee | |
| 5,144,962 A | 9/1992 | Counts | |
| 5,159,940 A | 11/1992 | Hayward et al. | |
| 5,190,060 A | 3/1993 | Gerding | |
| 5,224,498 A | 7/1993 | Deevi | |
| 5,249,586 A | 10/1993 | Morgan et al. | |
| 5,261,424 A | 11/1993 | Sprinkel, Jr. | |
| 5,285,798 A | 2/1994 | Banerjee | |
| 5,322,075 A | 6/1994 | Deevi | |
| 5,388,594 A | 2/1995 | Counts | |
| 5,438,978 A | 8/1995 | Hardester | |
| 5,497,791 A | 3/1996 | Bowen et al. | |
| 5,505,214 A | 4/1996 | Collins | |
| 5,591,368 A | 1/1997 | Fleischauer et al. | |
| 5,666,977 A | 9/1997 | Higgins | |
| 5,666,978 A | 9/1997 | Counts | |
| 5,730,158 A | 3/1998 | Collins | |
| 5,743,251 A | 4/1998 | Howell | |
| 5,746,251 A | 5/1998 | Bullard | |
| 5,799,663 A | 9/1998 | Gross | |
| 5,819,756 A | 10/1998 | Mielordt | |
| 5,878,752 A | 3/1999 | Adams et al. | |
| 5,894,841 A | 4/1999 | Voges | |
| 6,040,560 A | 3/2000 | Fleischhauer | |
| 6,041,789 A | 3/2000 | Bankert | |
| 6,095,153 A | 8/2000 | Kessler | |
| 6,164,287 A | 12/2000 | White | |
| 6,178,969 B1 | 1/2001 | St. Charles | |
| 6,196,218 B1 | 3/2001 | Voges | |
| 6,354,293 B1 | 3/2002 | Madison | |
| 6,357,671 B1 | 3/2002 | Cewers | |
| 6,443,146 B1 | 9/2002 | Voges | |
| 6,532,965 B1 | 3/2003 | Abhulimen | |
| 6,715,494 B1 | 4/2004 | McCoy | |
| 6,772,756 B2 | 8/2004 | Shayan | |
| 6,803,545 B2 | 10/2004 | Blake | |
| 6,810,883 B2 | 11/2004 | Felter | |
| 6,854,461 B2 | 2/2005 | Nichols | |
| 7,100,618 B2 | 9/2006 | Dominguez | |
| 7,131,599 B2 | 11/2006 | Katase | |
| 7,726,320 B2 | 6/2010 | Robinson | |
| 7,845,359 B2 | 12/2010 | Montaser | |
| 7,997,280 B2 | 8/2011 | Rosenthal | |
| 8,156,944 B2 | 4/2012 | Han | |
| 2003/0108342 A1 | 6/2003 | Sherwood et al. | |
| 2004/0261802 A1 | 12/2004 | Griffin et al. | |
| 2005/0016550 A1* | 1/2005 | Katase | 131/194 |
| 2005/0236006 A1 | 10/2005 | Cowan | |
| 2006/0196518 A1* | 9/2006 | Hon | 131/360 |
| 2007/0267031 A1* | 11/2007 | Hon | 131/273 |
| 2008/0257367 A1* | 10/2008 | Paterno et al. | 131/328 |
| 2008/0276947 A1 | 11/2008 | Martzel | |
| 2009/0095311 A1 | 4/2009 | Han | |
| 2009/0151717 A1 | 6/2009 | Bowen | |
| 2009/0188490 A1 | 7/2009 | Han | |
| 2009/0230117 A1 | 9/2009 | Fernando | |
| 2009/0260642 A1 | 10/2009 | Monsees | |
| 2009/0272379 A1 | 11/2009 | Thorens | |
| 2010/0031968 A1 | 2/2010 | Sheikh | |
| 2010/0126505 A1 | 5/2010 | Rinker | |
| 2010/0181387 A1 | 7/2010 | Zaffaroni | |
| 2010/0200008 A1 | 8/2010 | Teieb | |
| 2010/0242974 A1 | 9/2010 | Pan | |
| 2010/0307518 A1 | 12/2010 | Wang | |
| 2011/0005535 A1 | 1/2011 | Xiu | |
| 2011/0036346 A1 | 2/2011 | Cohen | |

FOREIGN PATENT DOCUMENTS

| | | |
|---|---|---|
| CN | 1135860 | 11/1996 |
| CN | 1106812 C | 10/1998 |
| CN | 2293957 Y | 10/1998 |
| CN | 97216131.7 | 10/1998 |
| CN | 1252961 A | 5/2000 |
| CN | 1530041 A | 9/2004 |
| CN | 2643681 | 9/2004 |
| CN | 2648836 | 10/2004 |
| CN | 1541577 A | 11/2004 |
| CN | 03111582.9 | 11/2004 |
| CN | 1575673 A | 2/2005 |
| CN | 2719043 * | 8/2005 |
| CN | 2719043 Y | 8/2005 |
| CN | 200420031182.0 | 8/2005 |
| CN | 2777995 Y | 5/2006 |
| CN | 101084801 | 12/2007 |
| CN | 200997909 Y | 1/2008 |
| CN | 10116542 A | 2/2008 |
| CN | 101176805 | 5/2008 |
| CN | 1196660 | 3/2010 |
| DE | 10051792 | 5/2002 |
| EP | 0057243 | 8/1982 |
| EP | 0230420 | 8/1987 |
| EP | 0295122 | 12/1988 |
| EP | 0295122 A2 | 12/1988 |
| EP | 0342538 | 11/1989 |
| EP | 0358002 | 3/1990 |
| EP | 0545186 | 6/1993 |
| EP | 0703735 | 4/1996 |
| EP | 0824927 A | 2/1998 |
| EP | 0845220 A1 | 6/1998 |
| EP | 0893071 A1 | 1/1999 |
| EP | 0970627 A1 | 1/2000 |
| EP | 0951219 | 11/2002 |
| EP | 1618803 A1 | 1/2006 |
| EP | 1736065 A1 | 12/2006 |
| GB | 1528391 A | 10/1978 |
| JP | 64000498 | 1/1989 |
| JP | 06114105 | 4/1994 |
| JP | 07506999 | 8/1995 |
| JP | 09075058 | 3/1997 |
| UA | 47514 | 12/1997 |
| WO | WO9409842 | 5/1994 |
| WO | WO9421317 | 9/1994 |
| WO | WO9740876 | 11/1997 |
| WO | WO9748293 | 12/1997 |
| WO | WO9817130 | 4/1998 |
| WO | WO0049901 | 8/2000 |
| WO | WO0050111 | 8/2000 |
| WO | WO0105459 | 1/2001 |
| WO | WO03034847 | 1/2003 |
| WO | WO03022364 | 3/2003 |
| WO | WO03055486 | 7/2003 |
| WO | WO03101454 | 12/2003 |
| WO | WO04001407 A1 | 12/2003 |
| WO | WO2004023222 | 3/2004 |
| WO | WO2004080216 | 9/2004 |
| WO | PCT/CN04/000182 | 11/2004 |
| WO | WO2004095955 | 11/2004 |
| WO | PCT/CN05/000337 | 8/2005 |
| WO | WO2005099494 | 10/2005 |
| WO | WO2006082571 | 8/2006 |
| WO | WO2007078273 | 7/2007 |
| WO | WO2007131449 | 11/2007 |
| WO | WO2007131450 | 11/2007 |
| WO | WO2008055423 | 5/2008 |
| WO | WO2008077271 | 7/2008 |
| WO | WO2008130813 | 10/2008 |
| WO | WO2009118085 | 10/2009 |
| WO | WO2009135729 | 11/2009 |
| WO | WO2010052323 | 5/2010 |
| WO | 2010091593 | 8/2010 |
| WO | 2010145468 | 12/2010 |
| WO | WO2010145805 | 12/2010 |
| WO | WO2011010334 | 1/2011 |
| WO | WO2011022431 | 2/2011 |

OTHER PUBLICATIONS

Australian Patent Office, Examination Report for SG 200505930-8, May 4, 2006.

Australian Patent Office; Exam Report for AU2004234199, Aug. 14, 2009.

Australian Patent Office; Search and Examination Report for SG200604498-6, Apr. 16, 2008.

Australian Patent Office; Singapore Examination Report for Singapore Patent Application No. 0604498-6 SG 200505930-8, May 13, 2008.
European Patent Office, extended European Search Report for EP 07721148, Dec. 6, 2010.
European Patent Office, extended European Search Report for EP 11001479, Jul. 4, 2011.
European Patent Office, Supplementary European Search Report for EP05729107, Jul. 31, 2007.
European Patent Office, Supplementary European Search Report for EP04718242, Jul. 27, 2007.
European Patent Office, Supplementary Partial European Search Report for EP04718242, May 22, 2007.
European Patent Office, Supplementary Partial European Search Report for EP05729107, May 22, 2007.
Introduction to Selecting and Using Electronic Components, ISBN7-111-13752-3.
Japanese Patent Office; Office Action for JP2006504199, Oct. 30, 2009 (with English translation).
Korean Patent Office; Notice of Preliminary Rejection for KR1020057009767, Jul. 27, 2009.
Macau Patent Office; Official Communication for MOI121, Apr. 17, 2009.
Malaysia Intellectual Property Office; Examiner's Report for Malaysian Application No. PI 20041407, Sep. 28, 2007.
Manual for Electric Engineers, 2nd Edition, Mar. 2000.
Manual for Mechanical Designers, 4th Edition, Jan. 2002.
Materials Manual—Nonmetal, Jul. 1985.
State Intellectual Property Office (China), English Translation of the Written Opinion for PCT/CN07/001575, Jul. 20, 2007.
State Intellectual Property Office (China), English Translation of the Written Opinion for PCT/CN07/001576, Aug. 3, 2007.
State Intellectual Property Office (China), International Search Report for International Application No. PCT/CN2004000182, Jun. 10, 2004.
State Intellectual Property Office (China), International Search Report for International Application No. PCT/CN2005/000337, Jul. 14, 2005.
State Intellectual Property Office (China), International Search Report for PCT/CN07/001575, Aug. 16, 2007.
State Intellectual Property Office (China), International Search Report for PCT/CN07/001576, Aug. 16, 2007.
Taiwan Intellectual Property Office; Official Letter for TW093111573, Apr. 24, 2009.
Ukrainian Patent Office; Examination Report for UA200511258, Feb. 4, 2009.
CN Creative ; INTELLICIG USA, *Ruyan v. Smoking Everywhere et al.* CV11-6268 Invalidity Contentions, Apr. 12, 2012.
Cyphert, GIL DBA NU1S, *Ruyan v. Smoking Everywhere et al.* CV11-0367 Invalidity Contentions, Apr. 11, 2012.
FIN Branding Group, LLC, Request for Inter Partes Reexamination of U.S. Patent No. 8,156,944, filed Sep. 13, 2012.
IP Australia, Patent Examination Report No. 1 for AU2007250367, Jul. 30, 2012.
IP Australia, Patent Examination Report No. 1 for AU2007250368, Aug. 9, 2012.
Sottera, Inc., *Ruyan v. Smoking Everywhere et al.* CV11-0367 Invalidity Contentions, Apr. 12, 2012.
Sottera, Inc., *Ruyan v. Smoking Everywhere et al.* CV11-0367 Invalidity Contentions, Exhibit 7 (Claim 20 Claim Chart), Apr. 12, 2012.
Sottera, Inc., *Ruyan v. Smoking Everywhere et al.* CV11-0367 Invalidity Contentions, Exhibit 8 (Claim 24 Claim Chart), Apr. 12, 2012.
State Intellectual Property Office, International Search Report for PCT/CN10/000125, Apr. 1, 2010.
State Intellectual Property Office International Search Report for PCT/CN10/073613, Aug. 26, 2010.
State Intellectual Property Office, Search Report for Utility Model Patent ZL 200620090805.0, Nov. 18, 2008.
United States Patent and Trademark Office, Office Action in Inter Partes Reexamination of U.S. Patent No. 8,156,944, mailed Nov. 27, 2012.
Machine translation Chinese Patent Application 200420031182 which corresponds to the priority document of WO20051099494 (Hon '494) Oct. 27, 2005, cited by the Examiner in the Nov. 27, 2012 Office Action identified above.
Machine translation of Chinese Patent Application 03111582.9 which corresponds to the priority document of WO2004/095955 (Hon '955) Nov. 11, 2004, cited by the Examiner in the Nov. 27, 2012 Office Action identified above.

* cited by examiner

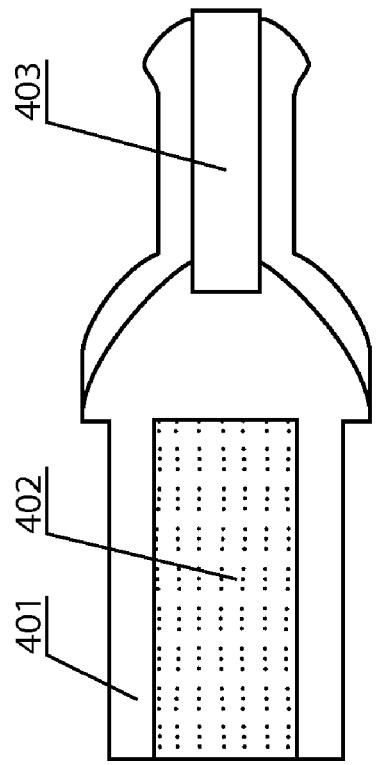
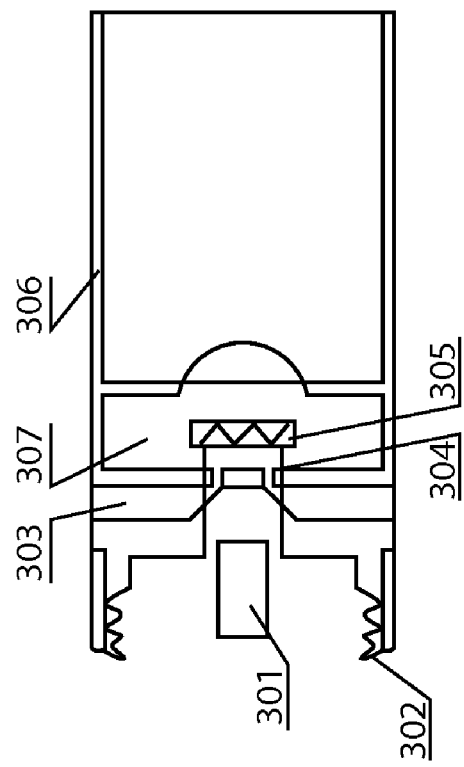
Figure 4
Figure 3

ELECTRONIC CIGARETTE

TECHNICAL FIELD

The invention relates to an electronic cigarette containing nicotine but not tar.

BACKGROUND ART

Today when it is known that "smoking is harmful to your health", there are still one billion people smoking cigarettes, and this figure is increasing every year. Although smoking causes serious respiratory system diseases and cancers, it is still difficult for smokers to completely quit smoking.

Nicotine is the active ingredient of a cigarette. During smoking, nicotine produces a lot of tar mist as the cigarette burns. The tar mist accesses the smoker's pulmonary alveolus and is quickly absorbed into the blood. Nicotine thus acts on the receptors of the smoker's central nervous system.

Nicotine is a micromolecular alkaloid, which is basically harmless to human bodies within a small dosage. Plus, the half life period of nicotine is extremely short in blood. Tar, on the other hand, is the major harmful substance in tobacco. Tobacco tar may include several thousands of ingredients, dozens of which are carcinogenic substances. Furthermore, it has been shown that second hand smoking is even more harmful to non-smokers.

Some cigarette substitutes do not contain harmful tar but do contain relatively pure nicotine. Such products include the "Cigarette Patch", "Nicotine Gargle", "Aerosol Packed in the High Pressure Tank with Propellant", "Nicotine Chewing Gum". These products are not as harmful as tar, but they are absorbed very slowly. As a result, the peak concentration of nicotine cannot be effectively established in blood, and the smokers are not satisfied in full. In addition, the substitutes do not satisfy the smokers "smoking" habit of repetitively inhaling and exhaling. Therefore, the substitute products are not effective as cigarette substitutes to quit smoking.

THE SUMMARY OF THE INVENTION

The purpose of this invention is to provide an electronic cigarette that substitutes for real cigarettes and helps smokers to quit smoking. For this invention, the aerosol may be regarded as liquid drops suspended in the air.

The present invention includes a battery assembly, an atomizer assembly and a cigarette bottle assembly. The battery assembly connects with one end of the atomizer assembly, and the cigarette bottle assembly is inserted into the other end of the atomizer assembly, thus forming one cigarette type or cigar type body.

The atomizer may be a capillary impregnation atomizer or spray atomizer, inside which there is a heating body. The said spray atomizer has a spray hole on it. The said spray hole is made of foamed ceramics, micro-porous ceramics, foamed metal, stainless steel fiber felt, or chemical fiber molding, which are drilled for holes. The said heating body is made of the micro-porous ceramics on which nickel-chromium alloy wire, iron-chromium alloy wire, platinum wire, or other electrothermal materials are wound. Alternatively, it may be a porous component made of electrically conductive ceramics or PTC ceramics and associated with a sintered electrode. The surface of the heating body is sintered into high-temperature glaze to fix the zeolite grains, which are made of natural zeolite, artificial non-organic micro-porous ceramics or aluminum oxide grains. The said cigarette bottle assembly includes the cigarette liquid bottle, fiber and suction nozzle. The fiber containing cigarette liquid is located on one end of the cigarette liquid bottle, and this end is inserted into the secondary shell and lies against the atomizer. The suction nozzle is located on the other end of the cigarette liquid bottle. Between the fiber and interior wall of the cigarette liquid bottle is an air intake hole. The said cigarette liquid bottle and suction nozzle are made of non-toxic plastic. The said fiber is made of polypropylene or nylon. The cigarette liquid in the said fiber for atomization contains 0.1-3.5% nicotine, 0.05-5% tobacco flavor, 0.1-3% organic acid, 0.1-0.5% stabilizer, and propanediol for the remaining. The said sucker and its connecting structure may be loaded with conventional drugs for delivery to the lung.

This invention will bring the following benefits and active effects: For this invention, smoking doesn't bring any cigarette tar, considerably reducing the carcinogenic risks. At the same time, the smokers can still enjoy the feel and excitement of smoking, and there is no fire hazard since there is no need for igniting. In addition, the unit and its connecting structure of this invention may also be loaded with conventional drugs for delivery to the lung.

DESCRIPTION OF DRAWINGS

FIG. 3 is the diagram of the diagram of the atomizer assembly of this invention.

FIG. 4 is the diagram of the cigarette bottle assembly of this invention.

SPECIFIC MODE FOR CARRYING OUT THE INVENTION

This invention is further described as follows on the basis of the drawings.

Example 1

Figure 1:
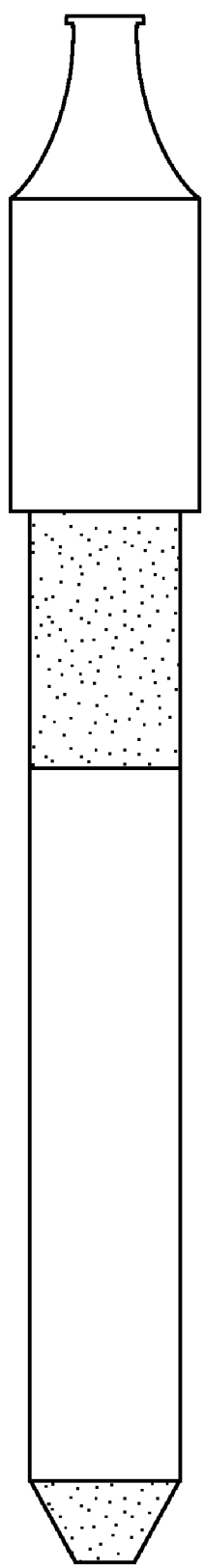
FIG. 1 is the visual appearance of the cigarette type of this invention.

As shown in FIG. 1, the visual appearance of this invention is similar to a cigarette inserted into the cigarette holder, and includes a battery assembly, an atomizer assembly and a cigarette bottle assembly. An external thread electrode (209) is located in one end of the battery assembly, and an internal thread electrode (302) is located in one end of the atomizer assembly. The battery assembly and atomizer assembly are connected through the screwthread electrode into an emulation cigarette. The cigarette bottle assembly is inserted into the other end of atomizer assembly, to form one cigarette type emulation aerosol sucker.

Figure 2A:
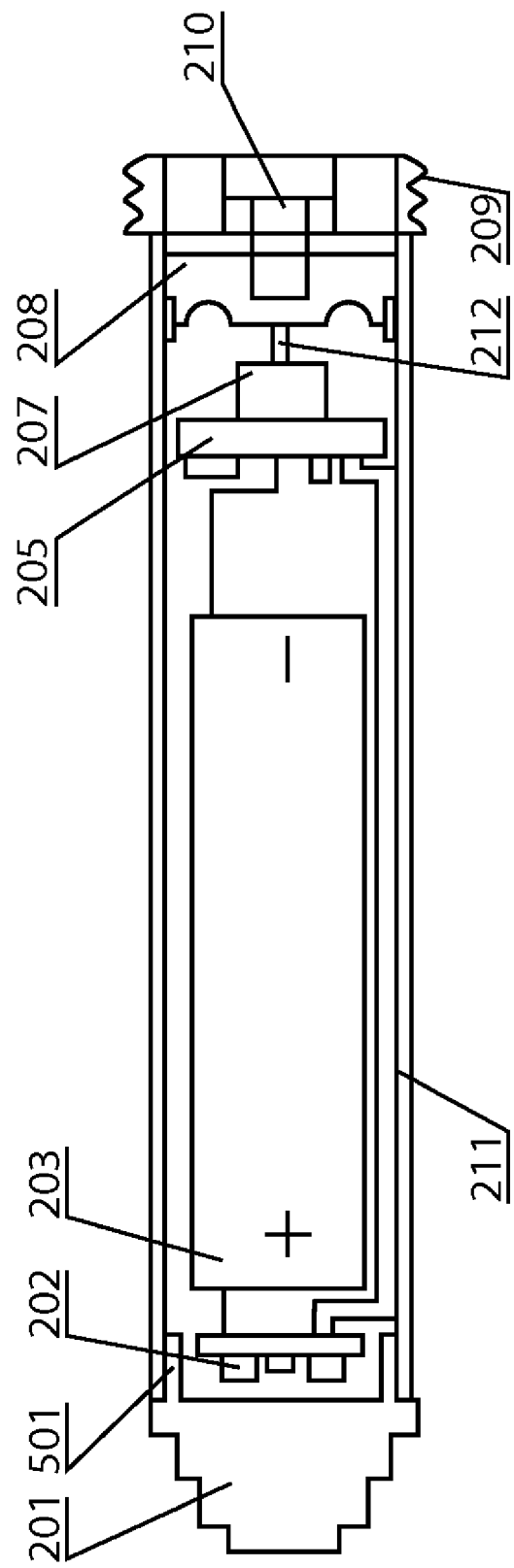
FIG. 2A is the diagram of one structure of the battery assembly of this invention.

As shown in FIG. 2A, the battery assembly includes the indicator (202), lithium ion battery (203), MOSFET electric circuit board (205), sensor (207), silica gel corrugated membrane (208), primary screwthread electrode (209), primary negative pressure cavity (210), and primary shell (211). On one end of the primary shell (211) is an external thread electrode (209), while on the other end is an indicator (202), where there is an indicator cap (201) on one side, in which there is a fine hole (501). On the other side, the lithium ion battery (203) and MOSFET electric circuit board (205) are connected successively. The sensor (207) is located on MOSFET electric circuit board (205). Between the primary screwthread electrode (209) and sensor (207) is a silica gel corrugated membrane (208), on which there is the primary negative pressure cavity (210). The sensor (207) is connected with the silica gel corrugated membrane (208) through the switch spring (212).

Therein, the sensor (207) may be switch sensor made of elastic alloy slice, Hall element of linear output, semiconductor force-sensitive chip, semiconductor matrix thermoelectric bridge chip, capacitance or inductance sensor. The indicators (202) include two red LEDs. The lithium ion battery (203) may be either a rechargeable polymer lithium ion battery or a rechargeable lithium ion battery. The external thread electrode (209) is a gold-coated stainless steel or brass part with a hole drilled in the center. The silica gel corrugated membrane (208) may alternatively be made of fluorinated rubber, butyronitrile rubber, or elastic alloy film.

As shown in FIG. 3, the atomizer assembly includes the internal thread electrode (302), air-liquid separator (303), atomizer (307) and the secondary shell (306). One end of the secondary shell (306) is inserted into the cigarette bottle assembly for connection, while the other end has an internal thread electrode (302), in which there is the secondary negative pressure cavity (301). The air-liquid separator (303) and the atomizer (307) are connected with the internal thread electrode (302) successively. On the secondary shell (306), there is an air intake hole (502). The air-liquid separator (303) is made of stainless steel or plastic with a hole drilled. The internal thread electrode (302) is a gold-coated stainless steel or brass part with a hole drilled in the center.

Figure 8:
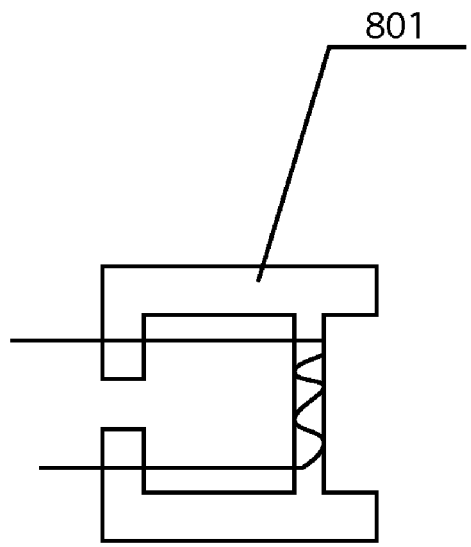
FIG. 8 is the diagram of the structure of the capillary impregnation atomizer of this invention.
Figure 9:
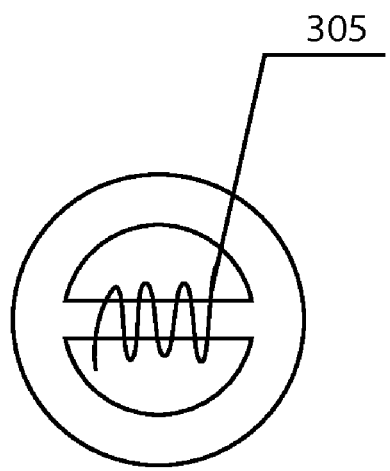
FIG. 9 is the left view of FIG. 8.
Figure 10:
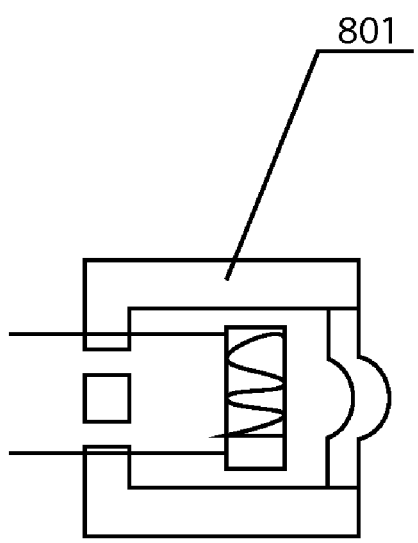
FIG. 10 is the diagram of the structure of the spray atomizer of this invention.
Figure 11:
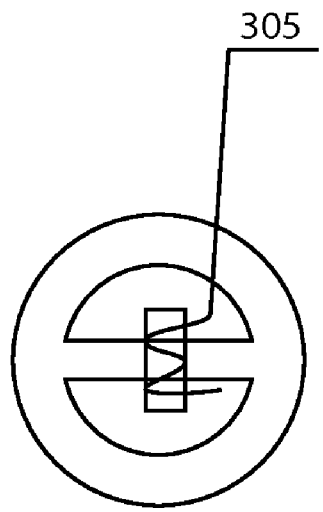
FIG. 11 is the left view of FIG. 10.

The atomizer (307) may be a capillary impregnation atomizer as FIGS. 8 and 9 show, or a spray atomizer as FIGS. 10 and 11 show. For this embodiment, it is a spray atomizer.

As shown in FIG. 4, the cigarette bottle assembly includes the cigarette liquid bottle (401), fiber (402) and suction nozzle (403). The fiber (402) containing cigarette liquid is located on one end of the cigarette liquid bottle (401), and this end is inserted into the secondary shell (306) and lies against the atomizer (307). The suction nozzle (403) is located on the other end of the cigarette liquid bottle (401). Between the fiber (402) and interior wall of the cigarette liquid bottle (401) is an air intake hole (503).

Figure 5A:
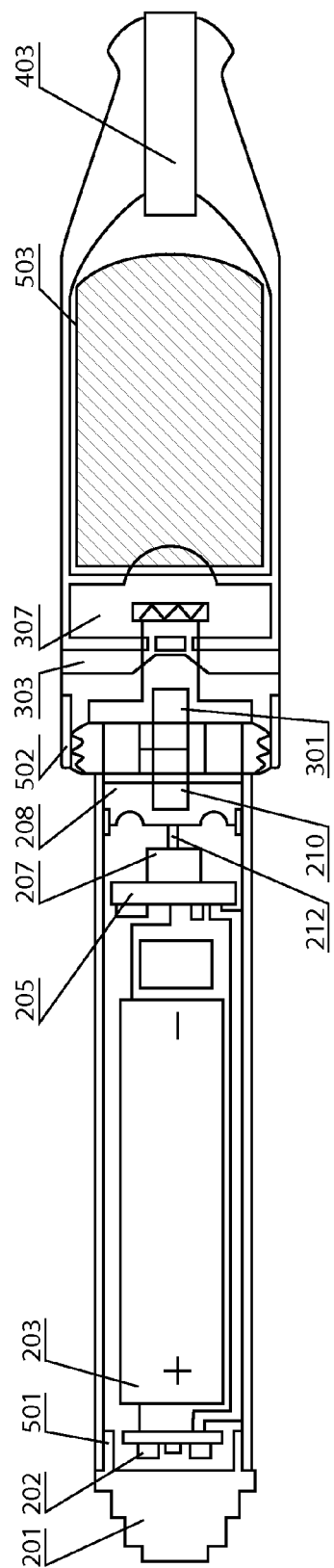
FIG. 5A is the diagram of one internal structure of this invention.

As shown in FIG. 5A, the standby state of this invention has the fully charged battery assembly shown on FIG. 2A fastened onto the atomizer assembly shown on FIG. 3, which is then inserted into the cigarette bottle assembly shown on FIG. 4. When the user slightly sucks the suction nozzle (403), the negative pressure forms on the silica gel corrugated membrane (208) through the air intake hole (503) and the primary and secondary negative pressure cavities (210, 301), the silica gel corrugated membrane (208), under the action of suction pressure difference, distorts to drive the switch spring (212) and sensor (207), thus invoking MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209), so that the heating body (305) inside the atomizer (307) produces heat. The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

When suction stops, the switch spring (212) and sensor (207) are reset; the atomizer (307) stops working; the indicators (202) gradually die down. When the operation times reaches the pre-set value, the atomizer (307) provides a work delay of 5-20 seconds per time, so as to remove the micro-dirt accumulated on the heating body (305).

Besides the micro-porous ceramics, the liquid supply material of the atomizer (307) may also be foamed ceramics, micro-porous glass, foamed metal, stainless steel fiber felt, terylene fiber, nylon fiber, nitrile fiber, aramid fiber or hard porous plastics. The heating body (305) is made of the micro-porous ceramics on which nickel-chromium alloy wire, iron-chromium alloy wire, platinum wire, or other electrothermal materials are wound. Alternatively, it may be a porous component directly made of electrically conductive ceramics or PTC (Positive Temperature Coefficient) ceramics and associated with a sintered electrode. The surface of the heating body (305) is sintered into high-temperature glaze to fix the zeolite grains, which are made of natural zeolite, artificial non-organic micro-porous ceramics or aluminum oxide grains. The cigarette liquid bottle (401) and suction nozzle (403) in the cigarette bottle assembly are made of non-toxic plastic, and inside them is the fiber (402) made of polypropylene fiber or nylon fiber to absorb cigarette liquid. In the battery assembly, there is a fine hole (501) on the indicator cap (201) for balancing the pressure difference on both sides of the silica gel corrugated membrane (208).

The cigarette liquid contains 0.1-3.5% nicotine, 0.05-5% tobacco flavor, 0.1-3% organic acid, 0.1-0.5% stabilizer, and propanediol for the remaining.

The primary and secondary shell (211, 306) of this invention are made of stainless steel tube or copper alloy tube with baked-enamel coating of real cigarette color.

Figure 12:
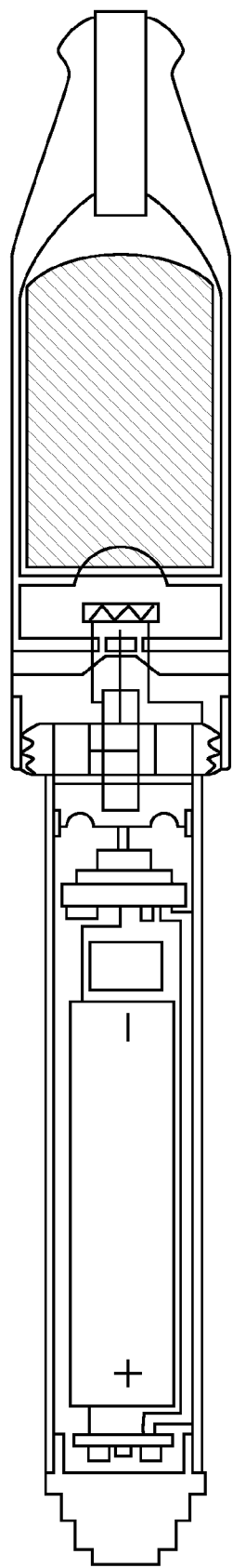
FIG. 12 is the diagram of the structure of the cigar type of this invention.

As shown in FIG. 12, this invention may have the diameter of the battery assembly increased in proportion, so that it is consistent with the diameter of the atomizer assembly. Its shell may be decorated with the leaf veins and sub-gloss brown-yellow baked-enamel coating, to create a cigar type emulation aerosol sucker.

For charging of the lithium ion battery (203) of this invention, the screwthread electrode (601) that matches the external thread electrode (209) on the battery assembly may be used as the charging interface.

Example 2

Figure 2B:
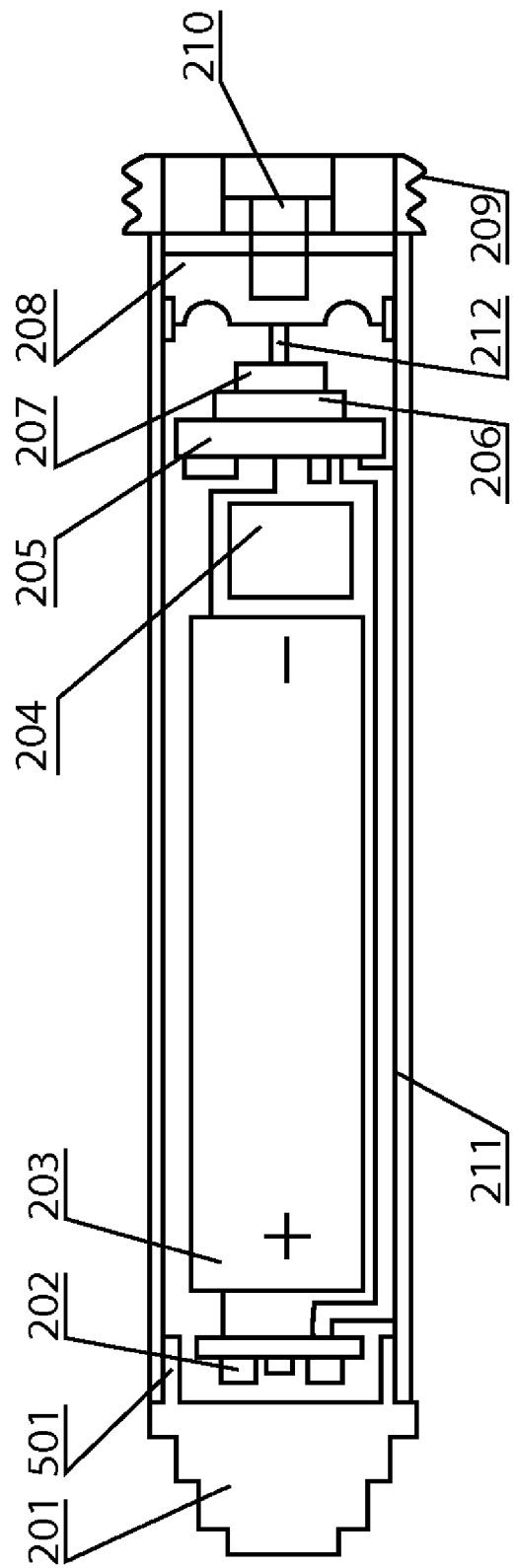
FIG. 2B is the diagram of another structure of the battery assembly of this invention.

As shown in FIG. 2B, the differences of this example from example 1 are as follows: MCU (206) is added between MOSFET electric circuit board (205) and sensor (207). On the surface of the primary shell (211), there is a screen (204) for display of the power of the lithium ion battery (203) and the sucking times.

Figure 5B:
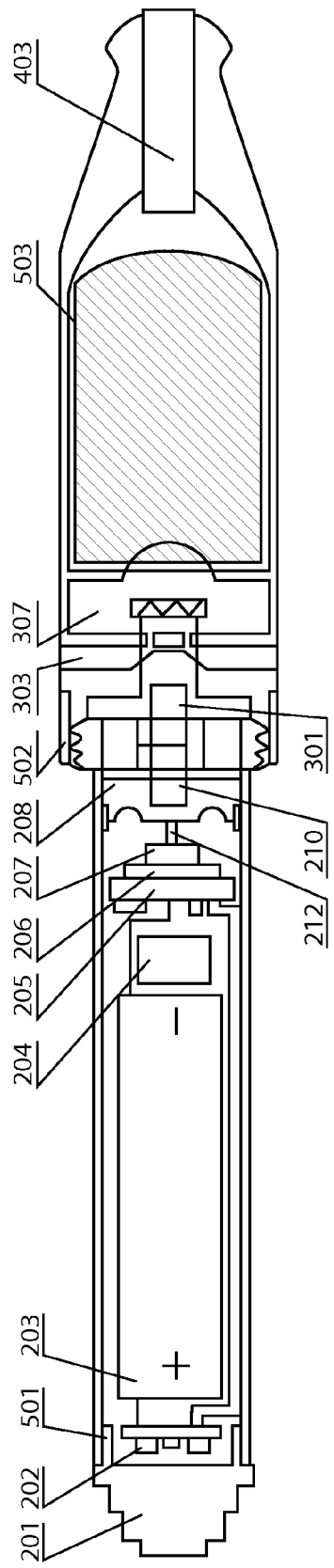
FIG. 5B is the diagram of another internal structure of this invention.
Figure 6:
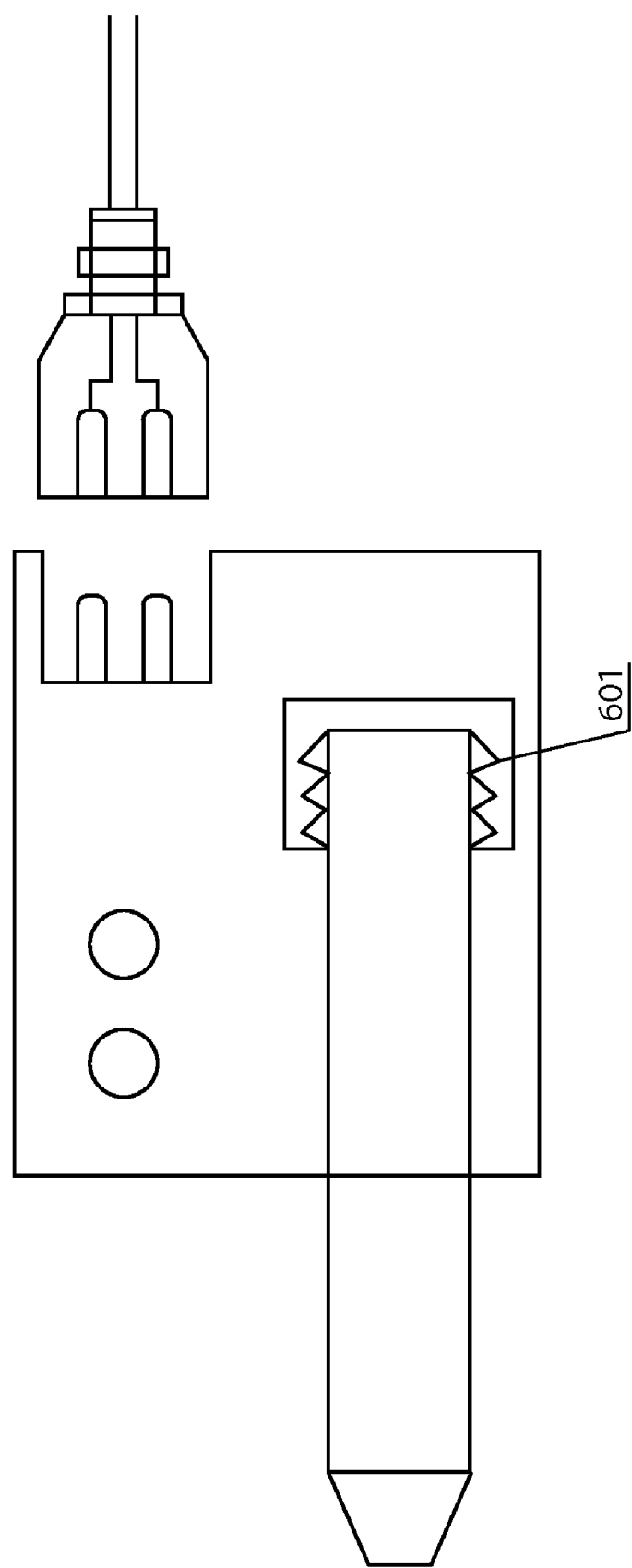
FIG. 6 is the diagram of the structure of the charger of this invention.

As shown in FIG. 5B, the standby state of this invention has the fully charged battery assembly shown on FIG. 2B fastened onto the atomizer assembly, which is then inserted into the cigarette bottle assembly shown on FIG. 4. When the user slightly sucks the suction nozzle (403), the negative pressure forms on the silica gel corrugated membrane (208) through the air intake hole (503) and the primary and secondary negative pressure cavities (210, 301), and the silica gel corrugated membrane (208), under the action of suction pressure difference, distorts to drive the switch spring (212) and sensor (207), thus invoking MCU (206) and MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209), so that the heating body (305) inside the atomizer (307) produces heat. The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

Figure 7:
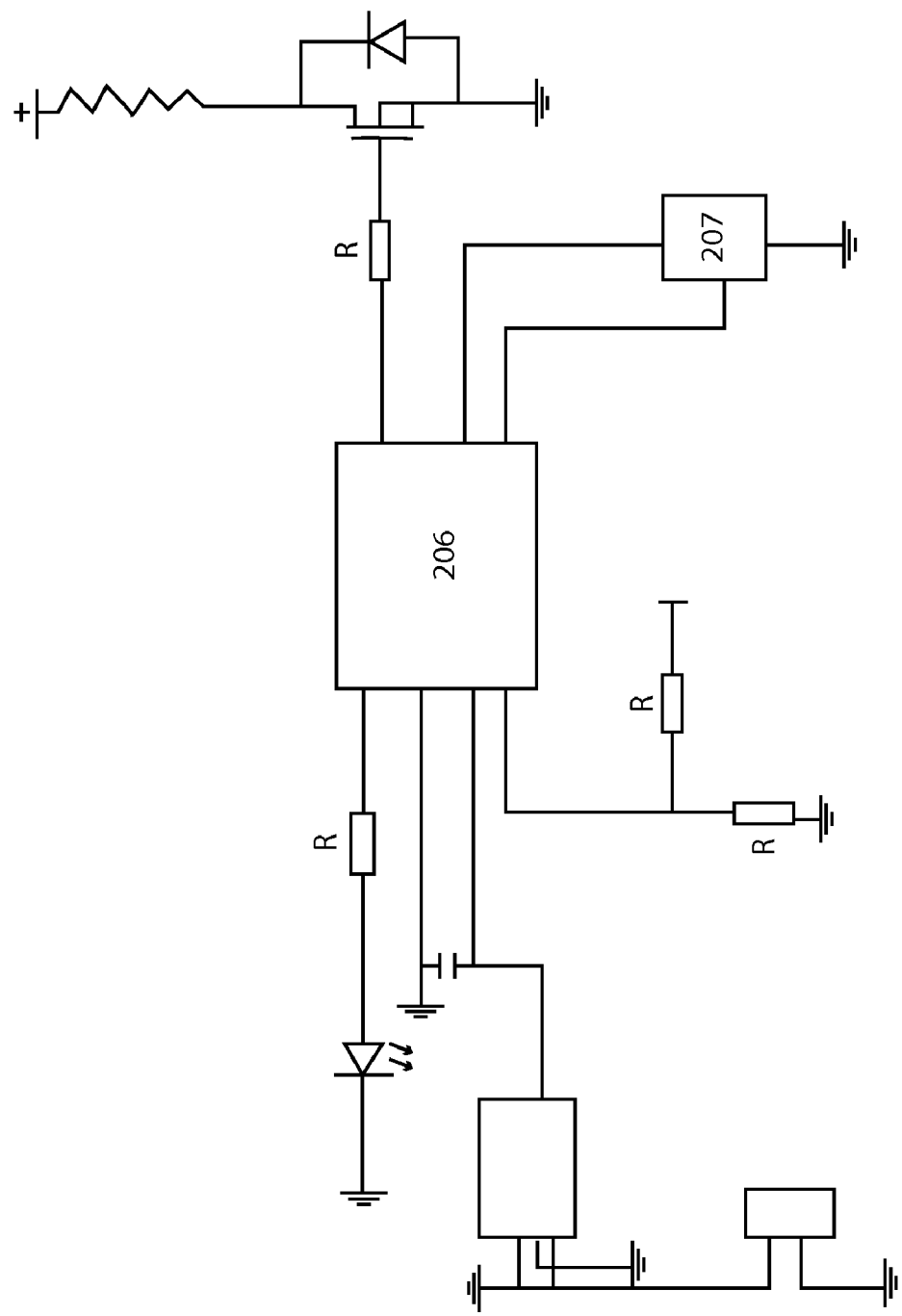
FIG. 7 is the electric circuit diagram of MCU and MOSFET of this invention.

As shown in FIG. 7, when the action of suction evokes the sensor, MCU (206) scans the sensor (207) in the power-saving mode of pulse, and according to the signal parameters of the sensor (207), restricts the atomizing capacity with the integral function of frequency to single operation time. Also, the MCU (206) accomplishes the pulse width modulation and over discharging protection for the constant power output, automatic cleansing for thousands of times per operation, step lighting/dying down control of the indicator, display of the operation times and battery capacity, automatic recovery after sensor malfunction shutdown, etc.

The unit and its connecting structure of this invention may also be loaded with drugs for delivery to the lung.

Above are just specifications of a concrete example and applied example of this invention. This doesn't necessarily restrict the scope of protection of this invention. Any equivalent modification or decoration made on the basis of the design spirit of this invention shall fall into the scope of protection of this invention.

The invention claimed is:

1. An electronic cigarette or cigar comprising:
a battery assembly comprising a battery assembly housing having a first end and a second end, with a battery, a micro-controller unit (MCU) and a sensor electrically connected to a circuit board within the battery assembly housing;
a primary screwthread electrode located on the first end of the battery assembly housing and having a hole through its center;
an atomizer assembly comprising:
an atomizer assembly housing having a first end and a second end;
an atomizer, and a solution storage area in the atomizer assembly housing;
a secondary screwthread electrode located on the second end of the atomizer assembly housing and having a hole through its center, the battery assembly and the atomizer assembly connected through the primary and secondary screwthread electrodes; and
with the atomizer including a heater coil wound around a porous component.

2. The electronic cigarette or cigar of claim 1, with the solution storage area in the solution assembly having a first end and a second end, and the second end of the solution assembly is inserted into the first end of the atomizer assembly housing.

3. The electronic cigarette or cigar of claim 1, wherein the primary screwthread electrode is an external screwthread electrode and the secondary screwthread electrode is an internal screwthread electrode.

4. The electronic cigarette or cigar of claim 1, wherein the battery assembly further comprises a membrane located between the primary screwthread electrode and the sensor.

5. The electronic cigarette or cigar of claim 1, further comprising a screen located on a surface of the battery assembly housing.

6. The electronic cigarette or cigar of claim 1, wherein the sensor comprises a switch sensor, a Hall element, a semiconductor force-sensitive chip, a semiconductor matrix thermoelectric bridge chip, a capacitance sensor or an inductance sensor.

7. The electronic cigarette or cigar of claim 1, wherein the atomizer assembly has an air intake hole at the secondary screwthread electrode.

8. The electronic cigarette or cigar of claim 1 further comprising a fiber material within the solution storage area.

9. The electronic cigarette or cigar of claim 1 with the porous component that the heater coil is wound around comprising a fiber material.

10. An electronic cigarette or cigar comprising:
a battery assembly housing having a first end and second end;
a battery connected to a circuit board within the battery assembly housing;
a primary screwthread electrode located on the first end of the battery assembly housing;
an atomizer assembly comprising:
an atomizer assembly housing having a first end and a second end;
a secondary screwthread electrode located on the second end of the atomizer assembly housing with the battery assembly and the atomizer assembly connected through the primary and secondary screwthread electrodes;
an atomizer in the atomizer assembly housing, with atomizer including a heater coil wound around a porous component; and
a solution assembly, which comprises, a suction nozzle at a first end of the solution assembly, and a solution storage area with a liquid containing fiber material in the solution storage area.

11. The electronic cigarette or cigar of claim 10 with the porous component that the heater coil is wound around comprising a fiber material.

12. The electronic cigarette or cigar of claim 10, wherein the second end of the solution assembly is inserted into the first end of the atomizer assembly, thus forming a cigarette or cigar body.

13. The electronic cigarette or cigar of claim 10, wherein the circuit board is a Metallic Oxide Semiconductor Field Effect Transistor (MOSFET) circuit board.

14. The electronic cigarette or cigar of claim 10, wherein the primary screwthread electrode is an external screwthread electrode and the secondary screwthread electrode is an internal screwthread electrode.

15. The electronic cigarette or cigar of claim 10, wherein the battery assembly further comprises a membrane located between the primary screwthread electrode and the sensor.

16. The electronic cigarette or cigar of claim 10, wherein the battery assembly further comprises a micro controller unit (MCU) electrically connected to the circuit board.

17. The electronic cigarette or cigar of claim 10, wherein the atomizer assembly has an air intake hole.

18. The electronic cigarette or cigar of claim 17, wherein the air intake hole is at the secondary screwthread.

19. The electronic cigarette or cigar of claim 10 wherein the coil comprises nickel-chromium alloy wire, iron-chromium alloy wire, platinum wire or another electrothermal material.

20. The electronic cigarette or cigar of claim 10 wherein the heating element comprises a plurality of zeolite grains.

21. The electronic cigarette or cigar of claim 10, wherein the primary screwthread electrode connects to a charger.

22. The electronic cigarette or cigar of claim 10 with at least one of the primary and the secondary screwthread electrodes having a hole through its center.

23. An electronic cigarette comprising:
battery assembly including a battery assembly housing having a front end and a back end, with a battery, a micro-controller unit (MCU) and a sensor electrically connected to a circuit board within the battery assembly housing;
a first screwthread electrode located on the back end of the battery assembly housing;
an atomizer assembly comprising:
an atomizer assembly housing having a front end and a back end;
an atomizer, and a solution storage area in the atomizer assembly housing;
a second screwthread electrode located on the front end of the atomizer assembly housing, the battery assembly and the atomizer assembly connected through the first and second screwthread electrodes; and
with the atomizer including a heater coil wound around a porous component.

24. The electronic cigarette of claim 23 with the solution storage area within a solution assembly, and with a front end of the solution assembly inserted into the back end of the atomizer assembly.

\* \* \* \* \*

UNITED STATES PATENT AND TRADEMARK OFFICE
CERTIFICATE OF CORRECTION

| | | |
|---|---|---|
| PATENT NO. | : 8,375,957 B2 | Page 1 of 1 |
| APPLICATION NO. | : 12/226819 | |
| DATED | : February 19, 2013 | |
| INVENTOR(S) | : Lik Hon | |

It is certified that error appears in the above-identified patent and that said Letters Patent is hereby corrected as shown below:

On the Title page of the patent, between (65) and (51), insert
-- (30) Foreign Application Priority Data
May 16, 2006    (CN) .................................. 200620090805 U --.

In the Claims:

In column 6, line 37, in claim 10, before "second" insert -- a --.

In column 8, line 2, in claim 23, before "battery assembly including" insert -- a --.

Signed and Sealed this
Second Day of July, 2013

Teresa Stanek Rea
*Acting Director of the United States Patent and Trademark Office*